US006613108B1

(12) United States Patent
Aittamaa et al.

(10) Patent No.: US 6,613,108 B1
(45) Date of Patent: Sep. 2, 2003

(54) PROCESS FOR PRODUCING A FUEL COMPONENT

(75) Inventors: Juhani Aittamaa, Helsinki (FI); Juha Jakkula, Kerava (FI); Petri Lindqvist, Porvoo (FI); Matti Koskinen, Helsinki (FI); Juha Linnekoski, Hyvinkää (FI); Outi Krause, Kauniainen (FI); Mauri Sourander, Helsinki (FI); Jyrki Ignatius, Porvoo (FI); Antti Pyhälahti, Helsinki (FI)

(73) Assignee: Fortum Oil & Gas Oy, Espoo (FI)

( * ) Notice: Subject to any disclaimer, the term of this patent is extended or adjusted under 35 U.S.C. 154(b) by 0 days.

(21) Appl. No.: 09/343,559

(22) Filed: Jun. 30, 1999

(30) Foreign Application Priority Data

Oct. 16, 1998 (FI) .................................................. 982250

(51) Int. Cl.⁷ .............................. C10L 1/18; C07C 2/74
(52) U.S. Cl. ........................ 44/449; 44/450; 585/255; 585/310; 585/316; 585/510; 585/520; 585/521; 585/526
(58) Field of Search ................. 585/514, 510, 585/515, 520, 525, 526, 529; 44/449, 451

(56) References Cited

U.S. PATENT DOCUMENTS

| | | | |
|---|---|---|---|
| 2,363,300 A | | 11/1944 | Dunstan et al. |
| 3,455,664 A | * | 7/1969 | Rosscup et al. ............... 44/451 |
| 3,474,151 A | * | 10/1969 | Grane ......................... 44/451 |
| 4,100,220 A | | 7/1978 | Bowman et al. |
| 4,375,576 A | | 3/1983 | Smith, Jr. |
| 4,447,668 A | | 5/1984 | Smith, Jr. et al. |
| 4,540,839 A | * | 9/1985 | Keyworth et al. .......... 585/520 |
| 4,704,482 A | * | 11/1987 | Sanderson et al. ............ 44/451 |
| 4,705,903 A | * | 11/1987 | Sanderson et al. ............ 44/451 |
| 5,227,534 A | * | 7/1993 | Harandi ....................... 585/331 |
| 5,723,687 A | | 3/1998 | Marchionna et al. |
| 5,877,372 A | | 3/1999 | Evans et al. |
| 5,908,964 A | * | 6/1999 | Koskinen et al. ........... 568/697 |
| 6,011,191 A | * | 1/2000 | Girolamo et al. ........... 585/514 |
| 6,242,661 B1 | | 6/2001 | Podrebarac et al. |
| 6,433,238 B1 | | 8/2002 | Di Girolamo et al. |

FOREIGN PATENT DOCUMENTS

| | | | |
|---|---|---|---|
| EP | 00 48893 | * | 4/1982 |
| EP | 0467345 A2 | * | 7/1991 |
| EP | 0745576 | | 12/1996 |
| GB | 522818 | | 6/1940 |
| GB | 2325237 | | 11/1998 |
| WO | 9313043 | | 7/1993 |

OTHER PUBLICATIONS

EP 48893AUPAB:19930915, Apr. 7, 1982, Abstract.
Naresh F. Shah et al, Reactive Polymers, 19 (1993) pp. 181–190.

* cited by examiner

*Primary Examiner*—Margaret Medley
(74) *Attorney, Agent, or Firm*—Birch, Stewart, Kolasch & Birch, LLP

(57) ABSTRACT

The invention relates to process for dimerizing olefinic hydrocarbon feedstock, to hydrocarbon compositions and to fuel components produced by the process. According to the invention, fresh olefinic hydrocarbon feedstock is fed to a reaction zone of a system including at least one reaction zone and at least one distillation zone. The olefinic hydrocarbon feedstock is contacted with an acidic catalyst in the presence of an oxygenate at conditions in which at least a part of the olefins dimerizes. The effluent from the reaction zone is conducted to the distillation zone where dimerized reaction product is separated from effluent, and at least one flow comprising oxygenate is withdrawn from the side of at least one distillation column. The flow is circulated from distillation zone back to dimerization. The reaction mixture is recovered and optionally hydrogenated to form a parafinic reaction product.

54 Claims, 9 Drawing Sheets

PROCESS FOR PRODUCING A FUEL COMPONENT

BACKGROUND OF THE INVENTION

1. Field of the Invention

The present invention concerns a process for dimerizing olefins. In particular, the present invention concerns a process for dimerizing $C_4$- and $C_5$-olefins.

The present invention also concerns new fuel components as well as novel hydrocarbon compositions.

2. Description of Related Art

The octane number of the automotive fuels is increased by adding components with a high octane number, such as methyl-tert-butylether, MTBE. Alternatively, $C_4$-alkylate or isomerates can be used. The alkylate is typically produced by alkylating isobutane and isobutene, whereby trimethylpentanes and dimethylhexanes are obtained. By dimerizing isobutene to iso-octene and hydrogenating it further to iso-octane the production of a component equal to or better than alkylate is possible.

$C_5$-fraction has previously been used for producing ethers, such as tert-amyl methylether, TAME or tert-amyl ethylether, TAEE. Both these ethers have been used together with or instead of MTBE to increase the octane number of the automotive fuels.

The octane numbers (Research Octane Number, RON and Motor Octane Number, MON) of iso-octane are by definition 100.

The present process can also be used to dimerize linear butenes or a mixture of isobutene and linear butenes. The octane numbers of the formed products are not as high as the octane numbers of iso-octane, but also these reaction products can be used as fuel components.

In the art a process is known, in which MTBE and iso-octene are produced simultaneously (EP-A-745576). According to the publication the molar ratio of alcohol and iso-olefin has to be below the stoichiometric ratio or in the range of 0.2–0.7. If the ratio is greater than 0.7, only less than 10 wt-% of dimer is formed. The preferred lower limit depends on the composition of the feed and the alcohol (methanol or ethanol) used. It is stated in the publication that the selectivity of the dimers increases, when the molar ratio increases, but the percentage of the dimers in the product decreases. In other words, the yield of dimers can not be increased, because the amount of MTBE would increase. In addition, there is no mention in the publication of the use of other oxygen containing components for inhibiting the side-reactions.

An other process for producing both $C_4$-oligomers and alkyl-t-butylether is known from EP-0 048 893. In the publication, a high feed ratio of alcohol and isobutene is used. In the publication a reference is made to the possibility of recycling the product in order to produce longer oligomers.

EP-publication 0 082 316 discloses a MTBE-process comprising a distillation column with a side reactor. The flow from the side reactor can be fed either to prereactors or back to the distillation column. In this case, too, the ratio of methanol and isobutene is close to stoichiometric and the purpose of the side reactor is to increase the conversion to MTBE.

It is known in the art that oxygen-containing molecules, such as methanol, MTBE, tert-butylalcohol (TBA) and water increase the dimer selectivity and thus decrease the selectivity of the trimerizing or tetramerizing reactions when dimerizing olefins in the presence of an ion-exchange resin catalyst. In that connection, we refer to what is stated in U.S. Pat. Nos. 4,375,576 and 4,100,220.

GB-application 2 325 237 discloses a process for selective dimerization of isobutene, in which primary alcohol and alkyl ether are fed to the process together with isobutene-containing hydrocarbon feed. The molar ratio of alcohol to isobutene is less than 0.2 in the feed. The molar ratio of alcohol and alkyl ether together to isobutene in the feed is more than 0.1. It is, however, stated in the publication that the best range of the latter molar ratio actually varies from between 0.2 and 0.6 to between 0.3 and 0.6 and between 0.5 and 0.7 depending on the composition of the hydrocarbon feed. Thus, the molar ratio in the feed is kept relatively small.

In prior art, no such process is known, which would allow for free selection of the product composition of the dimerizing unit and enable the production of either pure dimer or a mixture of dimer and ether in the same unit.

SUMMARY OF THE INVENTION

The objective of the present invention is to eliminate the problems of prior art and provide a novel process for dimerizing olefinic feedstocks.

The invention is based on the idea that the $C_4$- and $C_5$-olefins are dimerized in the presence of alcohol or another oxygenate in a reaction sequence comprising at least one distillation zone and at least one reaction zone. The reaction is carried out at conditions in which at least part of the olefins dimerize. The distillation zone is arranged after the reaction zone, and a flow comprising oxygenate, like, for example, alcohol, water or the product(s) of reaction(s) between alcohol or water and the olefin(s) present in the feed, or a mixture of any or all of these is circulated from the distillation zone back to the dimerization. The circulation flow(s) is (are) drawn from the side of at least one distillation column. The molar ratio of alcohol or other oxygenate and isobutene is adjusted to be small during the reaction, thus maintaining the rate of dimerization high.

According to another process according to the present invention, the sidedraw is directed to another reaction zone and the overhead product is circulated back to the dimerization.

The process according to the present invention can be used to produce dimerized products from feeds containing olefinic hydrocarbons selected from the group of linear butenes, isobutene and linear or branched $C_5$-olefins. Alternatively, the feed can comprise a mixture of any or all of the olefins listed above.

According to a first preferred embodiment of the invention, the hydrocarbon feed containing isobutene or linear butenes or a mixture thereof, is contacted with an acidic catalyst together with alcohol or other oxygenate in a reaction system comprising at least one reaction zone and at least one distillation zone. The conditions in said reaction zone are such that at least a part of the isobutene is dimerized to iso-octene. The flow from said reaction zone is introduced into a distillation zone, where the main part of the dimerized reaction product is separated. A sidedraw comprising alcohol, other oxygenate or the reaction product or a mixture thereof is circulated from the distillation zone back to the dimerization. With the help of the sidedraw the conversion of isobutene and the production of dimerized product is increased.

According to the first preferred embodiment, the hydrocarbon composition produced by the process of the present invention comprises at least 85 wt-%, preferably 90 wt-% iso-octene, 10–4 wt-%, in particular 10–6 wt-% trimers of isobutene, less than 1 wt-% tetramers of isobutene, 0.02–2 wt-%, typically 0.5–1.5 wt-% MTBE and 1 wt-% or less other hydrocarbons. When the composition is hydrogenated, an iso-octane composition useful as a fuel component is obtained.

According to a second preferred embodiment of the invention the hydrocarbon feed contains olefins selected from the group of linear and branched $C_5$-olefins, or a mixture thereof. Thus, the olefins typically present in the feed comprise linear 1-, 2- or 3-pentene, 2-methyl-1-butene, 2-methyl-2-butene and 3-methyl-1-butene.

According to the second preferred embodiment, the hydrocarbon composition produced by the process of the present invention comprises at least 65 wt-%, preferably at least 75 wt-%, $C_5$-dimers, 5–32 wt-% , preferably 5–28.5 wt-% olefin trimers, less than 1 wt-%, preferably less than 0.5 wt-% olefin tetramers, and 0.001–2 wt-%, preferably 0.001–1 wt-% oxygenate. Oxygenate can be for example MTBE or TBA, depending on the oxygenate used in the process. When the composition is hydrogenated, a composition useful as a fuel component is obtained.

According to third preferred embodiment of the invention the hydrocarbon feed contains olefins selected from the group of isobutene, linear butene, linear and branched $C_5$-olefins, or a mixture thereof. Thus, the olefins present in the feed possibly comprise any or every one of those described above.

According to the third preferred embodiment, the hydrocarbon composition produced by the process of the present invention comprises at least 65 wt-%, preferably at least 70 wt-% dimers or $C_9$-olefins, 5–32 wt-%, preferably 5–28.5 wt-% trimers, less than 1 wt-%, preferably less than 0.5 wt-% tetramers, 0.001–2 wt-%, typically 0.001–1 wt-% oxygenate. When the composition is hydrogenated, a composition useful as a fuel component is obtained.

Considerable advantages are achieved by means of the present invention. When using the process of the present invention, iso-olefins can be converted to their dimers or to tertiary ether almost completely. In addition, a more dimer selective process with a smaller alcohol feed than known in the art can be achieved, thus making the production more efficient compared with previously used processes.

With the aid of the invention an isobutene processing plant, such as MTBE-unit, can be modified to a dimerization unit without high expenses. Similarly, a $C_5$-olefin (e.g. isoamylene) processing plant, such as TAME unit can be modified to a dimerization unit. At the conditions where dimer is formed, the fraction containing ether or alcohol or a mixture thereof, is taken as a sidedraw from the distillation column and circulated back to the reaction zone. The ether or alcohol functions as an oxygen-containing component and decomposes in the reaction zone at least partly to alcohol and olefin. When all the ether is circulated back, then dimers and minor amounts of trimers and heavier hydrocarbons are produced, while if part of the ether is recovered, then alcohol is preferably added in order to maintain the conditions beneficial for dimer selectivity.

The conditions in the reaction zone can be optimized to match different production objectives. The process according to the present invention is suitable for dimerizing $C_4$-olefins, $C_5$-olefins or mixtures thereof. The switch from one product to another is simple, thus creating perfect flexibility to answer to the demands of the changing market.

With the aid of the recycling flow the temperature in the reactor can be slightly lowered compared to conventional etherification process. This is due to the fact that etherification is an exothermic reaction and less ether, including the undesired dimethyl ether, is formed since, according to the present invention, the methanol feed is smaller to begin with. The use of ethers as oxygenates is preferred in some cases, as the relatively high amount of alcohol in the first reaction zone easily reacts with the olefins to form the corresponding ether, and thus more heat is generated than when ether is the oxygenate originally fed to the reaction zone.

The rate of reaction can be increased by increasing the temperature in the process. This is especially preferred when TBA is used as the oxygenate.

The use of water as the oxygenate facilitates the separation, since the alcohol recovery unit is not needed. Furthermore, the amount of recycling flow decreases significantly compared with the use of primary alcohols. Further still, there will not form diethers of primary alcohols, which is a considerable advantage, since dialkyl ethers are light components for which is hard to find further use. All this is achieved with a very small amount of water.

The investment costs and the use of two separate distillation columns are much more expensive compared with a case where a sidedraw is taken from a distillation column. When only one column is used, the column has to be bigger, but savings are gained since the expensive parts, such as reboiler, condenser and instrumentation are not needed in duplicate.

Further, when considering retrofitting of plants, is much more easier to fit in only one column, possibly only modify an existing column, than try to make room enough for two columns instead.

The hydrocarbon composition obtained after hydrogenation of the reaction product of isobutene dimerization is better than the iso-octane produced conventionally by alkylation, since over 65 wt-%, typically more than 85 wt-% is 2,2,4-trimethylpentane, which has a beneficial influence on the octane number of gasoline.

The hydrocarbon compound obtained after hydrogenation of dimerized $C_5$-fraction contains predominantly tetramethyl hexane, which has the most beneficial influence on the octane number of gasoline of all the $C_{10}$ isomers.

In the conventional alkylation processes extremely acidic catalysts are used. Olefins react with acid forming red oil. Red oil is also called acid soluble oil, ASO. In alkylation processes, a liquid acidic catalyst, such as $H_2SO_4$ or HF is used. In the present invention, a solid catalyst is used and the oxygen-containing compound protects the catalyst.

DETAILED DESCRIPTION OF THE INVENTION

Definitions

Figure 1:
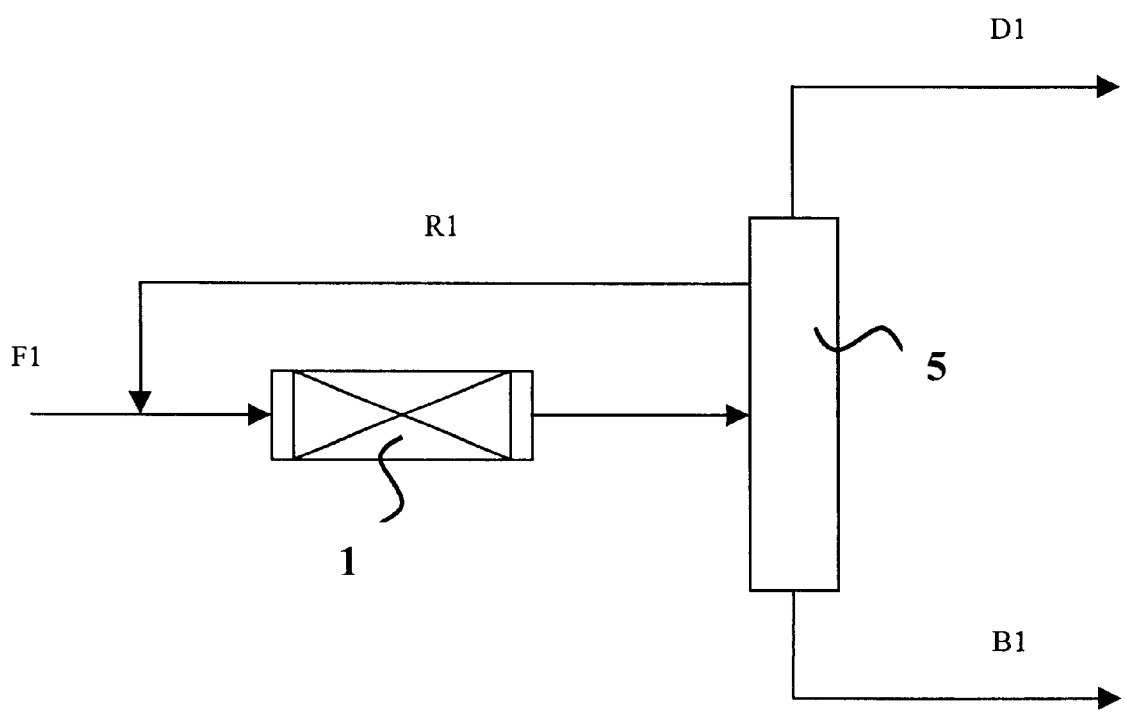
FIG. 1 depicts in a schematic fashion the process configuration of the basic technical solution of the invention, in which the fresh feed is fed to the process via a prereactor and a side flow is circulated from the distillation column back to the fresh feed.

For the purposes of the present invention, "distillation zone" designates a distillation system comprising one or more distillation columns. The columns are preferably connected in series. The feed plate can be selected for each column to be most advantageous in view of the overall process. Likewise, the plates for sidedraw of flows to be recovered or circulated can be selected individually for each column. The distillation column can be any column suitable for distillation, such as a packed column, or one provided with valve, sieve or bubble-cap trays.

A "reaction zone" comprises at least one, typically two or three, reactor(s). The reactor can be, e.g., a tubular reactor with multiple pipes, wherein the pipes are filled with catalyst. Other possibilities include a simple tubular reactor, a boiler reactor, a packed bed reactor and a fluidized bed reactor. The reactor used is preferably such in which the catalyst is placed in more than one layer and cooling is introduced between the layers. Preferably at least one of the reactors has a cooling system. For example, the pipes of the tubular reactor with multiple pipes can be cooled. Another example of a suitable reactor is a combination of a fixed bed reactor and a cooler, in which part of the reactor effluent can be circulated back to the reactor via the cooler. The operating pressure of the reactors depends on the type of the reactor and on the composition of the feed, typically it is desired to keep the reaction mixture in liquid phase.

"Oxygenate" designates a compound containing oxygen. Typically, the oxygenates used in the present invention are primary, secondary or tertiary alcohols or ethers, or water.

"Iso-octene" and "di-isobutene" are both products of isobutene dimerization. Thus they can be used interchangeably to designate 2,4,4-trimethyl-1-pentene and 2,4,4-trimethyl-2-pentene or a mixture thereof.

"Reaction mixture" contains the desired product of the dimerization reaction in the reaction zone. When only $C_4$-olefins or only $C_5$-olefins are fed to the process, it is clear that the resulting product of the mutual reactions of the olefins yield dimers. However, when both $C_4$- and $C_5$-olefins are present in the feed (the third embodiment), in addition to dimerization, also reactions between $C_4$-olefins and $C_5$-olefins yielding $C_9$-olefins can occur. The word "dimer" is also used for the reaction products in the specification for reasons of simplicity, but it is to be understood that when both $C_4$- and $C_5$-olefins are present in the feed, the reaction mixture typically contains also some amount of the $C_9$-olefins.

The Overall Process

According to the invention the hydrocarbon feed containing olefins is contacted with a catalyst together with alcohol or other oxygenate in a reaction zone at conditions in which at least a part of the olefins is dimerized. In case where the olefin feed comprises both $C_4$- and $C_5$-olefins, also reactions between different olefins occur, thus forming $C_9$-olefins. In addition also small amounts of other oligomers, such as trimers or tetramers are formed in the reaction. The flow from the reaction zone is introduced into a distillation zone, where the main part of the dimerized reaction product is separated.

A sidedraw comprising alcohol, other oxygenate and/or the reaction product is circulated from the distillation zone back to the reaction zone. With the help of the sidedraw the conversion of the olefin and the production of dimerized product is increased. It is to be understood, that although the following description refers to a sideflow in singular, which is the typical configuration, it is also possible to withdraw two or more sideflows containing oxygenate and circulate all those flows back to dimerization.

The invention is carried out, for example in an MTBE or TAME unit. Such a unit comprises a reaction zone, where the feed is contacted with a catalyst arranged in a solid bed. The flow from the reaction zone is conducted to a distillation zone, where components are separated.

The feed of the process according to the present invention is a hydrocarbon mixture containing olefins. The feed comprises olefins to be dimerized at least 10 wt-%, preferably at least approximately 20 wt-%. As already described, the olefins are selected from the group of linear 1- or 2-butene, isobutene and linear or branched $C_5$-olefins. Alternatively, the feed can comprise a mixture of any or every of the olefins listed above. Typically, the feed comprises dimerizable components; either $C_4$-olefins, preferably isobutene, whereby iso-octene is produced, or $C_5$-olefins, whereby substituted $C_{10}$-olefins are produced. It is clear that both $C_4$- and $C_5$-olefins can be present in the feed, whereby a great variety of products is produced. The composition of the product flow is discussed later.

According to the first preferred embodiment, in which $C_4$-hydrocarbons are dimerized, the hydrocarbon mixture in the feed comprises at least 10 wt-%, preferably at least approximately 20 wt-% isobutene. The feed can consist of pure isobutene, but in practice, the feedstock readily available comprises $C_4$-based hydrocarbon fractions from oil refining. Preferably, the feed comprises a fraction obtained from isobutane dehydrogenation, when the feed comprises mainly isobutene and isobutane and possibly small amounts of $C_3$- and $C_5$-hydrocarbons. Typically the feed then comprises 40–60 wt-% of isobutene and 60–40 wt-% isobutane, usually there is 5–20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert $C_4$-hydrocarbons and approximately 5 wt-% of $C_3$-, $C_5$- and heavier hydrocarbons altogether.

Due to the high isobutene content in the flow from the isobutane dehydrogenation the amounts of inert hydrocarbons in the recycling flows remain relatively small. The dehydrogenation fraction is very suitable for producing a product with a very high content of the dimerized isobutene.

The feed for producing iso-octene is also possible to select from the group containing $C_4$-fractions of FCC, TCC, DCC and RCC or from the $C_4$-fraction after the removal of butadiene, also called Raffinate 1 of an ethylene unit. Of these FCC, RCC, TCC and Raffinate 1 are preferred, since the hydrocarbon fractions can be used as such, possibly after removing the heavier ($C_{8+}$) fractions. Raffinate 1 is typically composed of approximately 50 wt-% isobutene, approximately 25 wt-% linear butenes and approximately 25 wt-% parafins. The product from the FCC is typically composed of 10–50, in particular 10–30 wt-% isobutene, 20–70 wt-% 1- and 2-butene and approximately 5–40 wt-% butane. As an example of a typical FCC-mixture, the following can be presented: approximately 30 wt-% isobutene, approximately 17 wt-% 1-butene, approximately 33 wt-% 2-butene and approximately 20 wt-% butane.

Also isobutene prepared from chemicals can be used as feed.

If the present invention is used for converting linear butenes, the linear butenes are preferably selectively isomerized to 2-butene as completely as possible. In this case, it is preferable to add a separate side reactor circulation to the process configuration. The temperature in this reactor is preferably higher than in the prereactor or circulation reactor in order to increase the conversion of dimerization.

FCC and corresponding hydrocarbon flows are suitable to use, e.g., in cases where the conventional MTBE unit is used to produce a product mixture comprising iso-octene and MTBE.

According to the second preferred embodiment of the invention, in which $C_5$-olefins are dimerized, the feed comprises olefins selected from the group of linear and branched $C_5$-olefins, or a mixture thereof. Thus, the olefins typically present in the feed comprise linear pentene, 2-methyl-1-butene, 2-methyl-2-butene, 3-methyl-1-butene or 2-ethylpropene. Also some amounts of $C_6$-olefins, typically at least 5 wt-% can be present in the feed.

Typically, the feed in the second preferred embodiment is FCC gasoline, light FCC gasoline, pyrolysis-$C_5$-gasoline, TCC gasoline, RCC gasoline and Coker gasoline, typically the $C_5$-fraction of FCC gasoline and can thus comprise also some $C_6$-olefins. Advantageously, the FCC fraction is fractionated to obtain as pure $C_5$-olefin fraction as possible where other $C_5$-hydrocarbons are present in less than 15 wt-%, preferably less than 5 wt-%. It is possible to use a fraction comprising also $C_6$-olefins. Typically, the feed then comprises 20 to 60 wt-%, in particular 30 to 50 wt-% $C_5$-olefins, 10 to 30 wt-%, in particular 15 to 25 wt-% $C_6$-olefins and 15 wt-% or less parafinic hydrocarbons pentanes.

According to the third preferred embodiment, the feed comprises both $C_4$- and $C_5$-olefins. In this case, the feed is typically selected from the group comprising FCC, TCC, DCC and RCC or from the $C_4$-fraction after the removal of butadiene, also called Raffinate 1 of an ethylene unit, FCC gasoline, light FCC gasoline, pyrolysis-$C_5$-gasoline, TCC gasoline, RCC gasoline and Coker gasoline. A fraction readily available comprises $C_4$ and $C_5$ fractions from FCC. Advantageously, a fraction comprising at least 10 wt-%, preferably at least 15 wt-% $C_4$-olefins and at least 10 wt-%, preferably at least 15 wt-% $C_5$-olefins is used. Typically the amounts of $C_4$-olefins and $C_5$-olefins are approximately equal, although a slight dominance of $C_4$-olefins in the fraction is also usual.

In addition to the hydrocarbon, an oxygen-containing compound (an oxygenate), such as alcohol, is fed into the process in order to slow down the oligomerization reactions of the olefin and to decrease the catalyst poisoning. Instead of alcohol, another possibility is to feed to the process a compound that will form alcohol. The use of oxygenate increases the dimer selectivity whereby the portion of trimers and tetramers of the olefin oligomers decreases. Thus, the fraction of dimers of the formed olefin oligomers is typically at least 80 wt-%. The oxygen containing (and alcohol forming) compound can be fed together with the fresh olefin feed, or it can be fed together with the circulation flow, or directly to the reaction zone.

The hydrocarbon feedstocks obtained from one of the oil refining unit operations described above usually contain water 50–500 ppm, in particular 100–300 ppm. In some cases, the water present in the hydrocarbon feedstock is enough to protect the catalyst and thus there is no need to feed additional oxygenate to the process. This is particularly true when the feed contains only $C_5$-olefins, or when the $C_4$-olefin content in the feed is less than 10 wt-%, in particular less than 5 wt-%. The presence of the oxygenate in the reaction zone in $C_5$-dimerization is necessary to protect the catalyst in the long run, while the selectivity of the reaction is relatively good even without the oxygenate.

According to the present invention, water, ether or alcohol, preferably $C_1$–$C_6$ alcohol (e.g. methanol, ethanol, isopropanol or t-butanol) is used as the oxygenate. As obvious from the list, the alcohol can be primary, secondary or tertiary alcohol. Further examples include tert-amyl methylether, 2-butanol and 2-pentanol.

Oxygenates, such as alcohol, protect the catalyst by hindering poisoning and the formation of large molecules, since the heavier components forming from trimers and tetramers block the catalyst. The molar ratio of oxygenate and olefin, e.g., alcohol and isobutene, in the feed is smaller than the stoichiometric ratio, preferably the ratio is kept below 0.2.

It is important to adjust the amount of oxygenate to the feedstock used. As already explained, an improvement of selectivity is needed for the reactions of $C_4$-olefins, while the importance of the oxygenate in the reactions of $C_5$-olefins lies in the protection of the catalyst. The catalyst, however, does need protection in the reactions of $C_4$-olefins as well. Based on the above, it is easily understood that the amount of oxygenate needed in the reactions of $C_5$-olefins is small, typically its content in the reaction zone is in the range of 50–500 ppm, in particular 100–300 ppm. It is thus possible that the desired amount of oxygenate is present in the hydrocarbon feed itself and therefore no additional oxygenate needs to be fed to the process. When the feed contains both $C_4$- and $C_5$-olefins, typically the amount of oxygenate needed increases as the fraction of $C_4$-olefins increases.

According to a preferred embodiment, water is fed to the process. It is to be understood, that water may be fed to the process in every one of the embodiments described above and below. Water reacts with iso-olefin(s) and forms tertiary alcohol, for example, tert-butyl alcohol, TBA in the reaction between water and isobutene or tert-amyl alcohol in the reaction between water and 2-methyl-1-butene or 2-methyl-2-butene. The reaction between water and linear olefin(s) produces secondary alcohols. Thus, for example the reaction between water and 2-butene results in sec-butyl alcohol. When the feed comprises different olefins, also mixtures of the above described alcohols are obtained.

According to one alternative, an alcohol which reacts with one or more of the olefins present in the feed is used. These alcohols are, for example, methanol and ethanol. Mixtures of ethers and dimers are obtained from the reactions between methanol or ethanol and iso-olefins. Alternatively, an alcohol which does not significantly react with the olefins, such as TBA, is fed to the process.

According to the invention, an acidic catalyst is used. Preferably, ion-exchange resins are used, for example such as are used for etherification. As catalysts can, however, be used zeolites and other inorganic catalysts. Thus, the resin can comprise sulphonic acid groups and it can be prepared by polymerizing or copolymerizing aromatic vinyl compounds and, thereafter, sulphonating. As examples of aromatic vinyl compounds the following may be mentioned: styrene, vinyl toluene, vinyl naphthalene, vinyl ethyl benzene, methyl styrene, vinyl chlorobenzene, and vinyl xylene. An acidic ion-exchange resin contains typically approximately 1.3 . . . 1.9, even up to 2 sulphonic acid groups per an aromatic group. Preferred resins are those based on copolymers of aromatic monovinyl compounds and aromatic polyvinyl, in particular divinyl, compounds, in which the concentration of polyvinylbenzene is approximately 1 . . . 20 wt-% of the copolymer. The particle size of the ion-exchange resin is preferably approximately 0.15 . . . 1 mm.

In addition to the resins already described, also perfluorosulphonic acid resins consisting of copolymers of sulphonylfluorovinyl ethyl and fluorocarbon compounds can be used.

Various suitable ion-exchange resins are commercially available, an example of these is Amberlyst 15.

The concentration of the catalyst is typically 0.01–20%, preferably approximately 0.1–10% of the weight of the liquid mixture to be handled.

The temperature of the reaction zone is typically 50–120° C. The upper level of the temperature range is set by the heat-resistance properties of the catalyst. The reaction can very well be carried out at temperatures higher than 120° C., for example up to 160° C. or even higher. The formation of the dimers can be enhanced by increasing the temperature during the reaction. On the other hand, a lower temperature favours the formation of ether.

The flow from the reaction zone is conducted to a distillation zone, where components are separated from one another. From the distillation zone, a sidedraw comprising alcohol or ether or the mixture thereof is withdrawn. When using alcohol which does not significantly react with the olefin (such as TBA), the sidedraw comprises a major part of the alcohol present in the reactor effluent. When using alcohol which does react with the olefin (such as methanol with isobutene), the sidedraw can comprise both alcohol and ether. Typically the sidedraw comprises ether up to 80 wt-%.

In the case where water is fed to the process, or when water is present in the hydrocarbon feedstock, water reacts with olefin(s) fed to the process as described above and the sidedraw comprises, depending on the feed, mixtures of water and alcohols formed in the reaction between water and the olefin(s) present in the feed. Possible compositions of the sidedraw comprise thus, for example, water, tert-butyl alcohol or tert-amyl alcohol, secondary alcohols or a mixture of any or all of these.

The sidedraw is typically taken from a plate higher than the feed plate. The sidedraw is circulated back to dimerization. The amount of the circulated flow can be altered as well as the point to which it is conducted (for example, either to the reaction zone or to the fresh feed). The mass flow of the circulated flow is typically 0.01 . . . 10 times, preferably 1 . . . 5 times the mass flow of fresh hydrocarbon feed.

The oxygenates form readily azeotropes with the olefins present in the feed. For example, TBA forms an azeotrope with iso-octene. The azeotropes can be decomposed by the addition of another compound, which forms an azeotrope with the oxygenate more readily than the olefin. The azeotrope-breaking compound can also be present in the feed originally, and thus no special feed is required. In this case, the azeotrope-breaking compound only has to be kept in the circulation and not taken out from the reaction system. A good example of this kind of compound are $C_6$-hydrocarbons, which break the TBA-iso-octene described above, thus enabling the recovery of the desired product iso-octene. As discussed, $C_6$-olefins are typically present in the $C_5$-fraction of FCC.

The dimerized reaction product is obtained as the bottoms product from the distillation zone. The product flow typically contains olefin oligomers (dimers and trimers). When isobutene is used as the dimerized olefin, the weight ratio of dimers to trimers in the bottoms product is, e.g., 99:1 . . . 80:20.

The composition of the product flow depends on the process parameters and on the composition of the feed. As already discussed, the process of the present invention can be used for producing dimerized product from olefinic feedstock. The olefins present in the feed can be either $C_4$-olefins, $C_5$-olefins or a mixture of these both. Thus it is clear that the composition of the product flow depends essentially on the fraction used as the feedstock.

According to the first preferred embodiment, $C_4$-olefins are dimerized. The compositions of the feed have already been discussed, and product compositions then are as follows:

When mainly dimers of isobutene are produced, they are typically present in the product flow in at least 85 wt-%, preferably at least 90 wt-%. Other components typically present in the product flow are MTBE, less than 2 wt-%, preferably less than 1 wt-%, trimers of isobutene, 10 wt-% or less, preferably 8 wt-% or less, tetramers of isobutene in less than 0.2 wt-% and other hydrocarbons in less than 1 wt-%. preferably less than 0.1 wt-%.

Regardless of the aimed product composition most (65–100 wt-%, typically 85–100 wt-%, preferably 95–100 wt-%) of the dimers produced by the process are 2,4,4-trimethyl pentenes. When the product stream is hydrogenated, a mixture comprising iso-octane is obtained. The fraction of other trimethyl pentanes (e.g. 2,3,4-trimethyl pentane) as well as the fraction of dimethyl hexanes in the mixture remains extremely small. Thus the octane number (RON) of the fuel component is high, typically at least 95, preferably approximately 98–100.

According to the second preferred embodiment, dimers Of $C_5$-olefins are produced. The product is typically as follows:

At least 65 wt-%, preferably at least 70 wt-%, $C_5$-dimers, 5–32 wt-%, preferably 5–28.5 wt-% olefin trimers, less than 1 wt-%, preferably less than 0.5 wt-% olefin tetramers, and 0.001–2 wt-%, preferably 0.001–1 wt-% oxygenate. Oxygenate can be for example MTBE or TBA, depending on the oxygenate used in the process. When the composition is hydrogenated, a composition useful as a fuel component is obtained.

Regardless of the aimed product composition most (65–100 wt-%, typically 85–100 wt-%, preferably 95–100 wt-%) of the dimers produced by the process are 3,3,4,4-tetramethylhexenes. When the product stream is hydrogenated, a mixture comprising 3,3,4,4-tetramethylhexanes is obtained. The fraction of other $C_{10}$-isomers in the mixture remains extremely small.

According to the third embodiment, dimers of both $C_4$- and $C_5$-olefins are produced. In addition also $C_4$- and $C_5$-olefins react and form $C_9$-olefins. The product composition then comprises at least 65 wt-%, preferably at least 70 wt-%, $C_5$-dimers, $C_4$-dimers and $C_9$- olefins, 5–32 wt-%, preferably 5–28.5 wt-% olefin trimers, less than 1 wt-%, preferably less than 0.5 wt-% olefin tetramers, and 0.001–2 wt-%, preferably 0.001–1 wt-% oxygenate. Oxygenate can be for example MTBE or TBA, depending on the oxygenate used in the process. When the composition is hydrogenated, a composition useful as a fuel component is obtained.

Regardless of the aimed product composition most (50–100 wt-%, typically 60–100 wt-%, preferably 90–100 wt-%) of the dimers and $C_9$-olefins produced by the process are iso-octene, tetramethylpentenes and trimethylhexenes. When the product stream is hydrogenated, a mixture comprising corresponding hydrogenated hydrocarbons is obtained. The relative abundance of individual components vary depending on the ratio of the reactive $C_4$- and $C_5$-components in the feed and on the oxygenate concentration present in the feed. When the product stream is hydrogenated, a mixture comprising iso-octane, tetramethylpentanes and trimethylhexanes is obtained. Thus the octane number (RON) of the fuel component is high, typically at least 95, preferably approximately 98–100.

The dimer fraction of the reaction product for a feed comprising (among other, less reactive compounds) both $C_4$- and $C_5$-iso-olefins (in a ratio 45:55) includes trimethylpentenes 20–30 wt-%, in particular 25–28 wt-%, tetramethylpentenes 20–30 wt-%, in particular 20–25 wt-%, tetramethylhexenes 4–8 wt-%, in particular 5–6 wt-%, and trimethylheptenes 2–5 wt-%, in particular 3–4 wt-%. The rest of the dimer product is less branched olefins.

Preferred process configurations are presented in the following.

According to a preferred embodiment of the invention (FIG. 1), the olefins are dimerized in a process comprising at least one reactor and at least one distillation column arranged after the reactor. Said reactor also functions as a prereactor, and thus the olefin-containing hydrocarbon flow is fed directly to the reactor.

Figure 2:
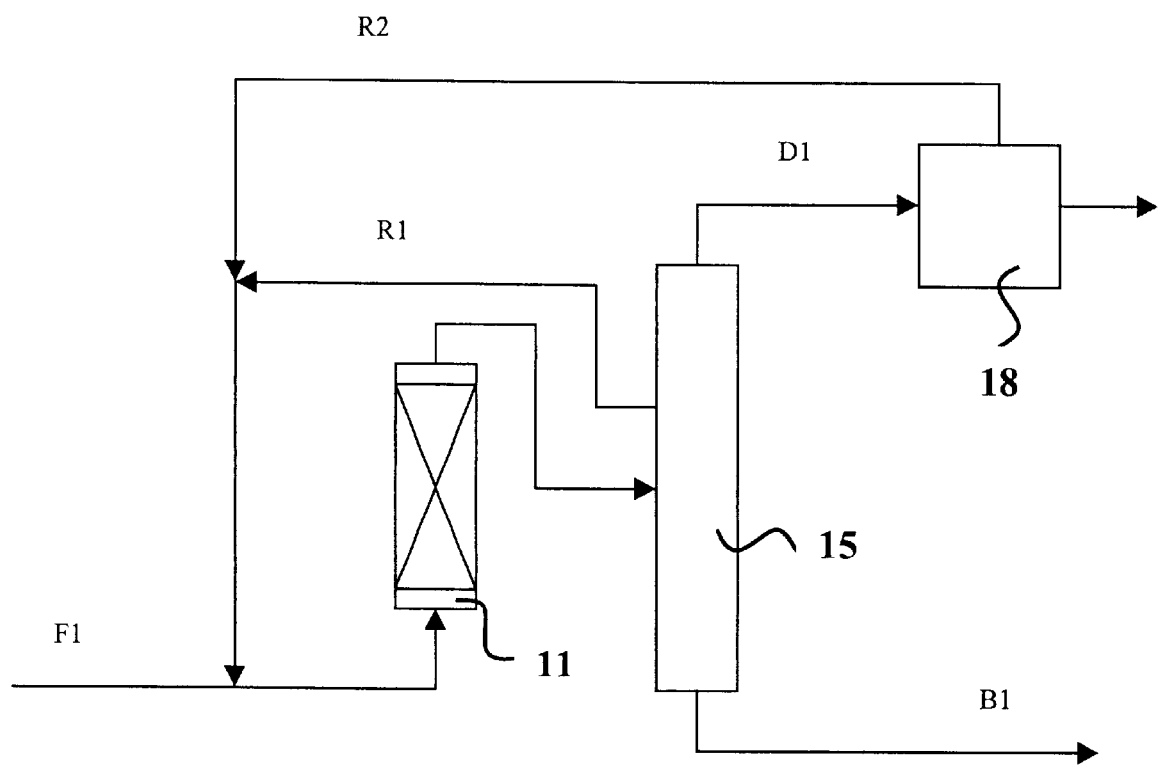
FIG. 2 depicts an embodiment in which an alcohol recovery unit is added to the process presented in FIG. 1.

According to another preferred embodiment (FIG. 2), alcohol and unreacted hydrocarbons are recovered as the overhead product of the distillation zone. The overhead product is conducted to alcohol recovery, from where alcohol is circulated back to the dimerization.

Figure 3:
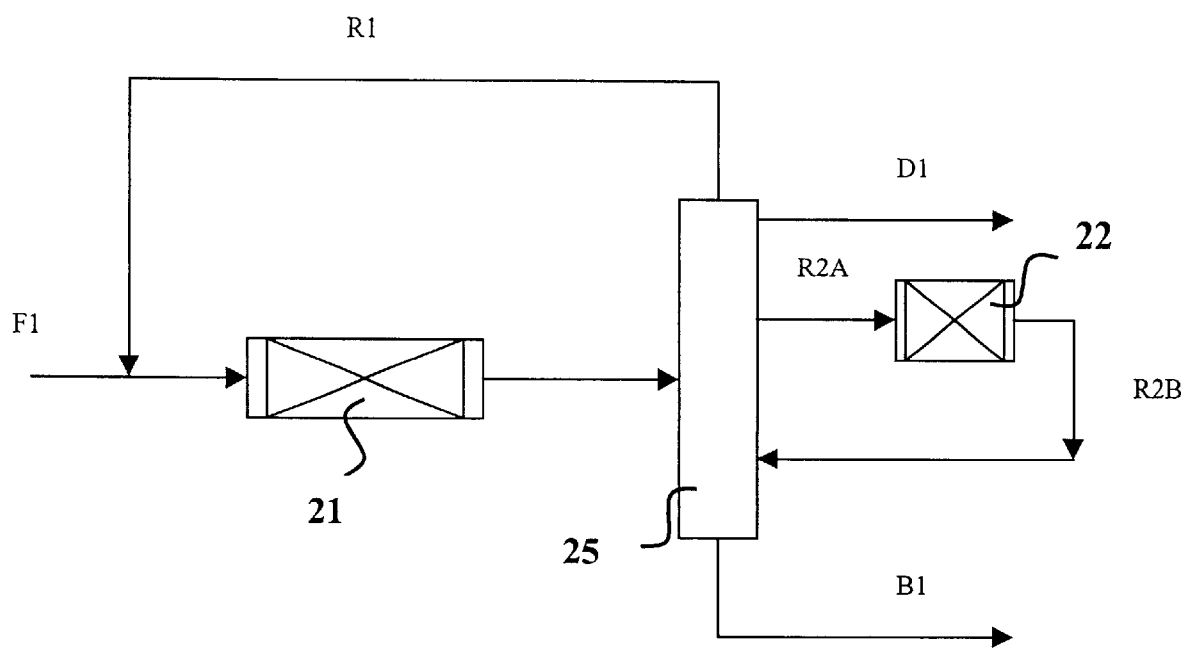
FIG. 3 depicts an embodiment in which there is a recycle flow to the prereactor from the distillation column and an additional side reactor.

According to still another preferred embodiment ethanol or methanol is used as the alcohol, and in addition to the dimerization of isobutene, said alcohols also react with the olefins forming alkyl ether. The formation of dimers can be enhanced by increasing the temperature during the reaction. The fraction with great amounts of ether is taken as a sidedraw from the distillation column and circulated back to the reaction zone. Ether functions as the oxygen-containing compound and decomposes partly to alcohol and olefin in the reactor. If all the ether is circulated back to the reaction zone, the bottoms product of the distillation zone comprises iso-octene (FIG. 3). Catalyst can be placed inside some of the distillation columns presented above in order to increase the conversion of olefin, whereby the formation of ether is increased.

According to still another preferred embodiment both dimerized olefin and alkyl ether are produced in the process. In this case, the olefin and alcohol have to react with each other. Thus, for example isobutene and methanol or ethanol are fed to the process. The decreasing of the reaction temperature during the reaction enhances the formation of tertiary ether. A mixture comprising iso-octene and tertiary ethers, the weight fraction of iso-octene of the isobutene reaction products being 20–95 wt-%, is recovered as the bottoms product of the distillation zone. If the tertiary ether is removed from the process, it is necessary to feed more alcohol in order to maintain reaction conditions suitable for the dimerization reaction. Alcohol can be fed either directly to the reaction zone or together with the fresh feed.

According to still another preferred embodiment the conditions in the reactors can be optimized in every situation. In the production of only dimer and trimer it is preferable to use a higher temperature (80–120° C.) than when producing also tertiary ether (50–70 ° C.).

In the attached drawings the alternative embodiments of the invention are illustrated in detail. Of the reference numbers 1, 11, 21, 22, 23, 31, 32, 33, 41, 42, 43, 51, 52, 61, 62, 71, 72, 81, 82 and 91 designate a reactor, 5, 15, 25, 35, 36, 37, 45, 46, 55, 56, 65, 66, 75, 76, 77, 85, 86 and 95 designate a distillation column, and 18 designates an alcohol recovery unit. The meanings of other notations become apparent from the specification which follows.

The basic idea of the process is presented in FIG. 1. The olefin-containing fresh feed F1 is introduced via a reactor 1 to a distillation column 5. The feed plate is in the middle part of the column. The process parameters in the distillation column are such that a zone with large amounts of ether and alcohol are formed into the middle part of the column. Tertiary ether and alcohol are drawn off from side of the column and circulated back to the fresh feed as circulation flow R1. Oligomers of the olefin are recovered as the bottoms product B1 of the distillation column. When isobutene is used as the olefin in the fresh feed, iso-octene is produced by the process. Iso-octane is produced by hydrogenating the iso-octene obtained by the process as described above.

The amount of the circulation flow is preferably 1 . . . 5 times of the amount of the fresh feed. The aim is to get the ether to the circulation as completely as possible, whereby the bottoms product B1 would comprise almost solely olefin oligomers.

According to another preferred embodiment, a recovery unit for alcohol is added to the basic process. This kind of a process is described in FIG. 2. The overhead product D1 of the distillation column 15 is conducted to the alcohol recovery unit, where alcohol is separated from unreacted hydrocarbons and conducted back to the fresh feed as a circulation flow R2.

The process configuration of still another preferred embodiment is presented in FIG. 3. According to the embodiment, ethanol or methanol is used as alcohol and an iso-olefin, e.g., isobutene, is used as olefin, since ethanol and methanol both react with isobutene to form tertiary ether. A fraction containing large amounts of ether is taken from the distillation column 25 and introduced to a side reactor 22. In the sidereactor, the ether is decomposed to alcohol and olefin. The flow D1 drawn from the upper part of the distillation column comprises predominantly lighter hydrocarbons. The overhead product of the distillation column R1 also comprises lighter hydrocarbons, and alcohol. The overhead product R1 is circulated back to dimerization. The product flow is recovered as bottoms product of the distillation column, from where it is conducted to hydrogenation.

Figure 4:
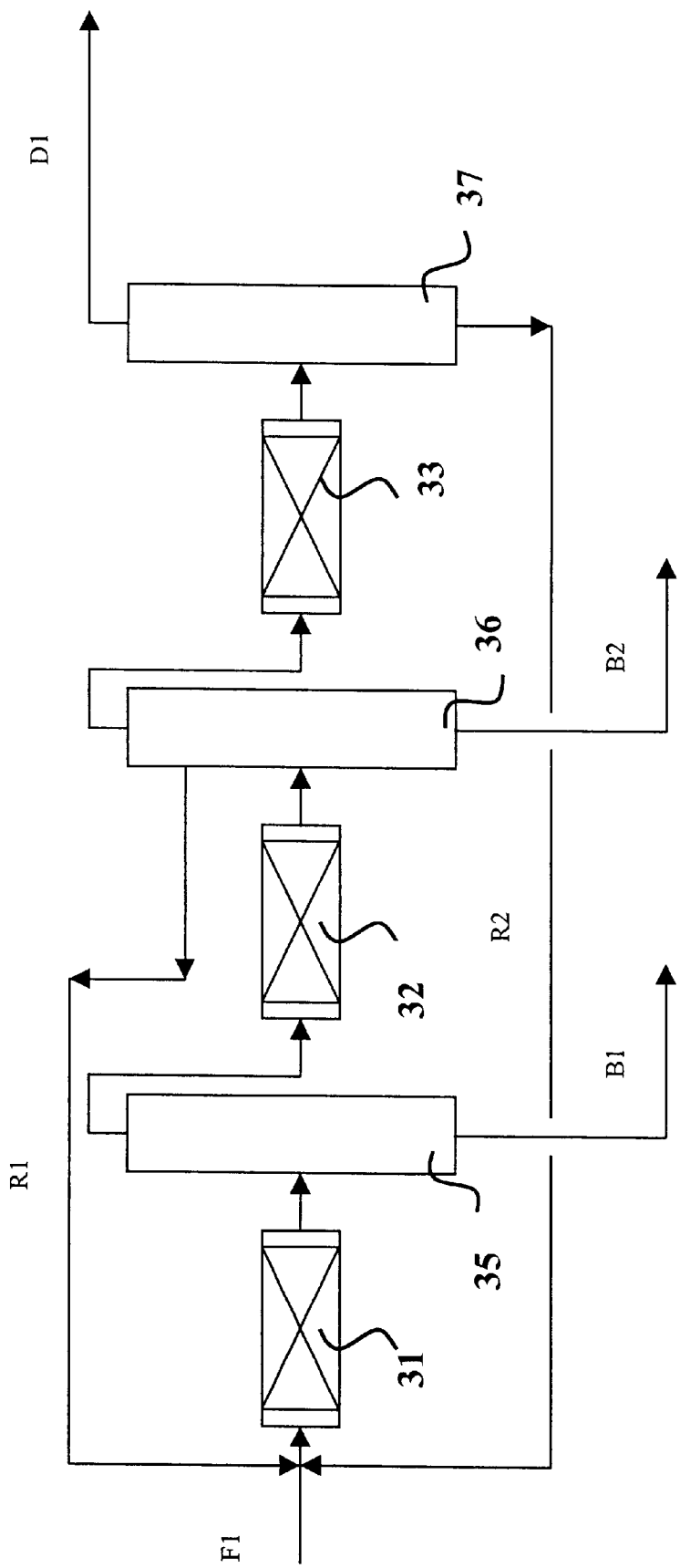
FIG. 4 depicts an embodiment, wherein the dimers are removed at relatively early stage and a flow is conducted from the distillation column back to the fresh feed.

The process can also be carried out with the configuration presented in FIG. 4. In this embodiment dimers are removed from the process at a relatively early stage. According to the embodiment the fresh feed is introduced via a prereactor 31 to a first distillation column 35. The bottoms product B1 of the first distillation column containing dimerized olefin(s) is conducted to hydrogenation and the overhead product is introduced to a second reactor 32. The effluent from the second reactor 32 is conducted to a second distillation column 36. The bottoms product of the second distillation column B2 containing dimerized olefin(s) is also conducted to hydrogenation. A flow R1 is drawn from the side of the second distillation column 36 and circulated back to the fresh feed. R1 comprises mainly inert hydrocarbons and ether. The overhead product of the second distillation column 36 is introduced further to a third reactor 33, the effluent of which is conducted to a third distillation column 37. The bottoms product R2 of the third distillation column is circulated back to the fresh feed. The overhead product of the third distillation column comprises predominantly inert hydrocarbons.

Figure 5:
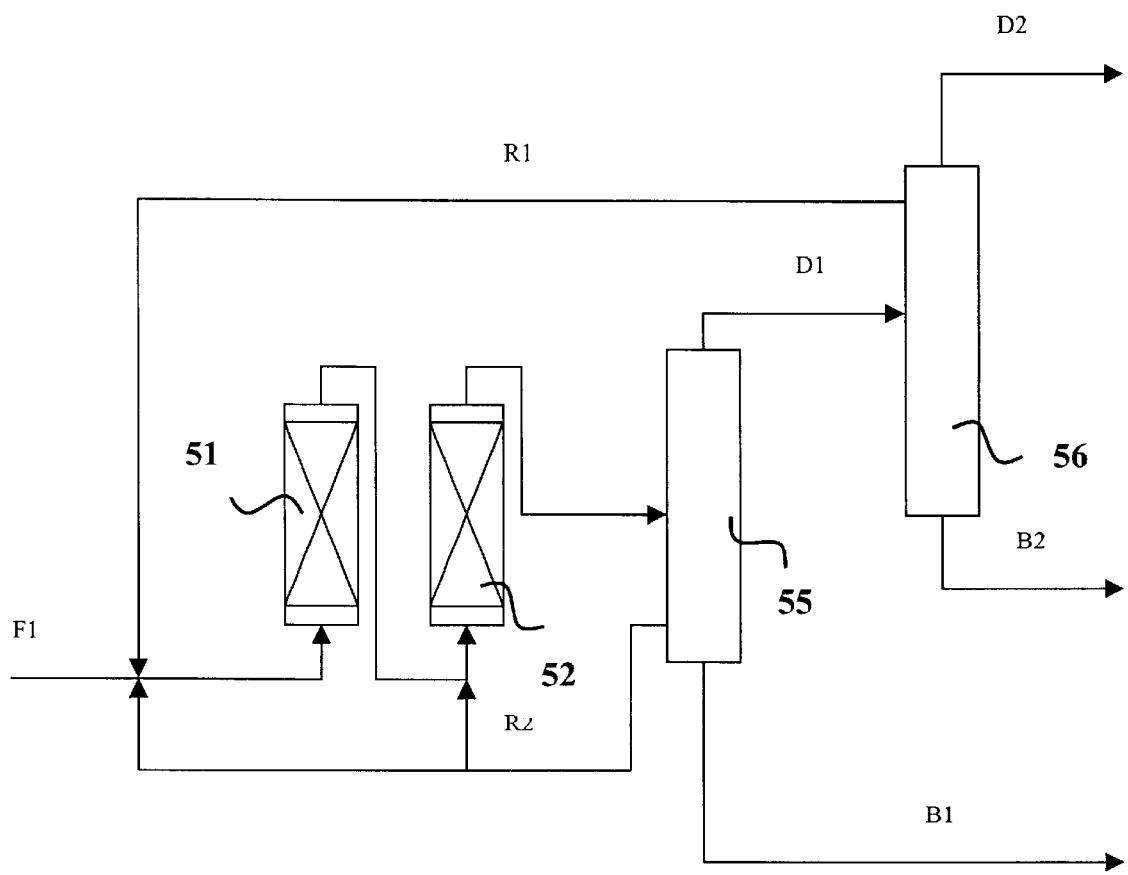
FIG. 5 depicts an embodiment in which there are two distillation columns after the reactors, and a sidedraw from both of the distillation columns is circulated back to the dimerization.

According to another alternative embodiment the separation zone is divided into two parts, of which the first separates the heavier components (ethers and oligomers) from light hydrocarbons and the latter part separates alcohol and $C_3$-hydrocarbons from each other. The process according to this embodiment is depicted in FIG. 5. Fresh feed F1 is conducted via two reactors 51, 52 to a first distillation column 55. A flow R2 comprising the ether-containing fraction is drawn from the side of the first distillation column 55. R2 is circulated back to the process so that it will be fed either before or in between the two reactors 51, 52. The bottoms product B1 of the first distillation column 55 contains olefin oligomers and ethers. The overhead product D1 of the first distillation column 55 is introduced to a second distillation column 56. An alcohol-containing flow R1 is drawn from the side of the second distillation column 56. The bottoms product B2 of the second distillation column 56 comprises unreacted $C_4$-hydrocarbons and the overhead product of the second distillation column 56 comprises $C_3$-hydrocarbons.

Figure 6:
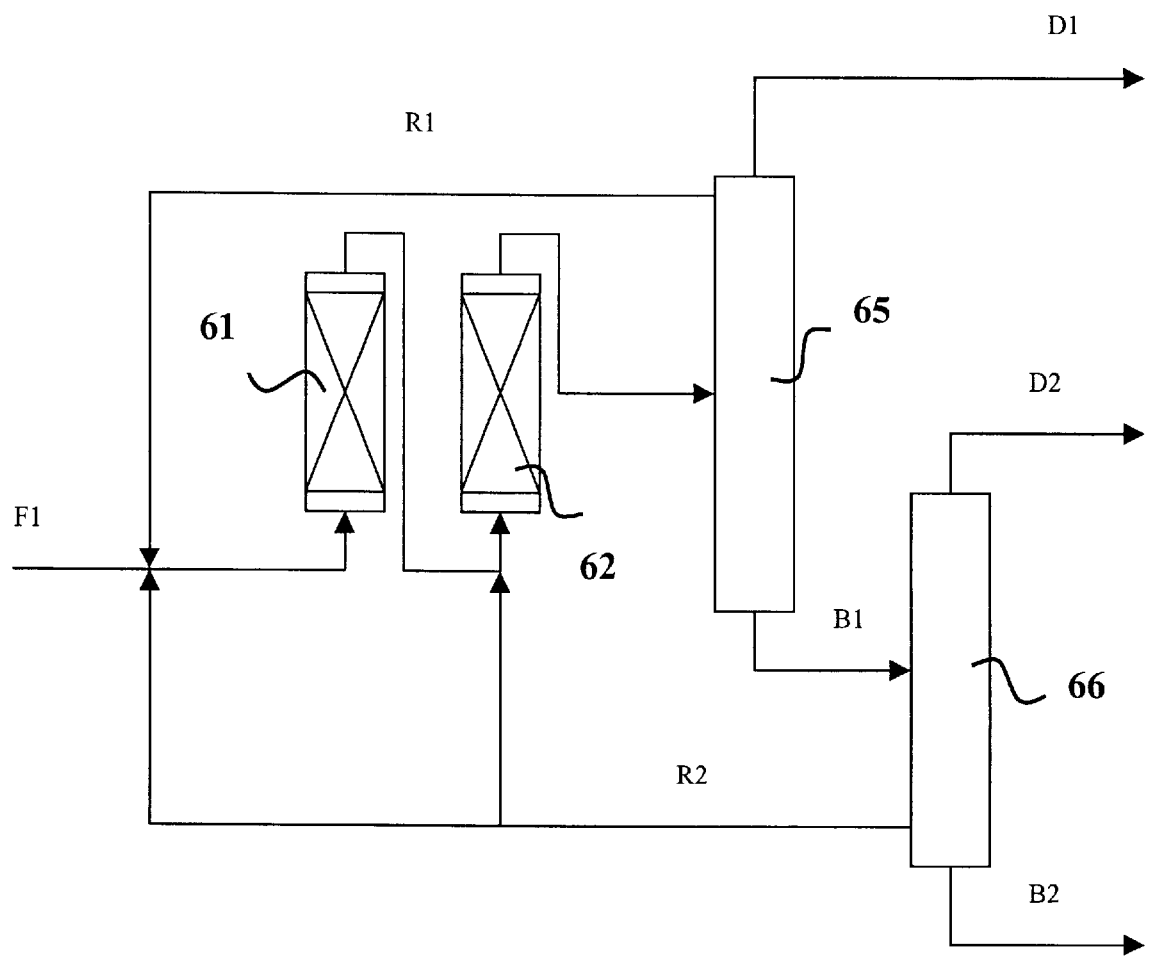
FIG. 6 depicts a variation of the embodiment presented in FIG. 5, in which the components are separated in a different order.

A variation of the embodiment described above is presented in FIG. 6. In the process the separation is conducted in another order and thus lighter $C_3$-hydrocarbons are fractionated to the overhead product D1 of the first distillation column 65 and the bottoms product B1 comprises heavier hydrocarbons. A flow R1 comprising alcohol is drawn from the side of the first distillation column 65 and circulated back to the fresh feed F1. Unreacted $C_4$-hydrocarbons are fractionated to the overhead D2 of the second distillation column 66 and as bottoms product B2 are obtained olefin oligomers, which are conducted to hydrogenation. From the side of the second distillation column is drawn a flow R2 comprising large amounts of ether. R2 is circulated back to the dimerization by feeding it either before or in between the reactors 61, 62.

Figure 7:
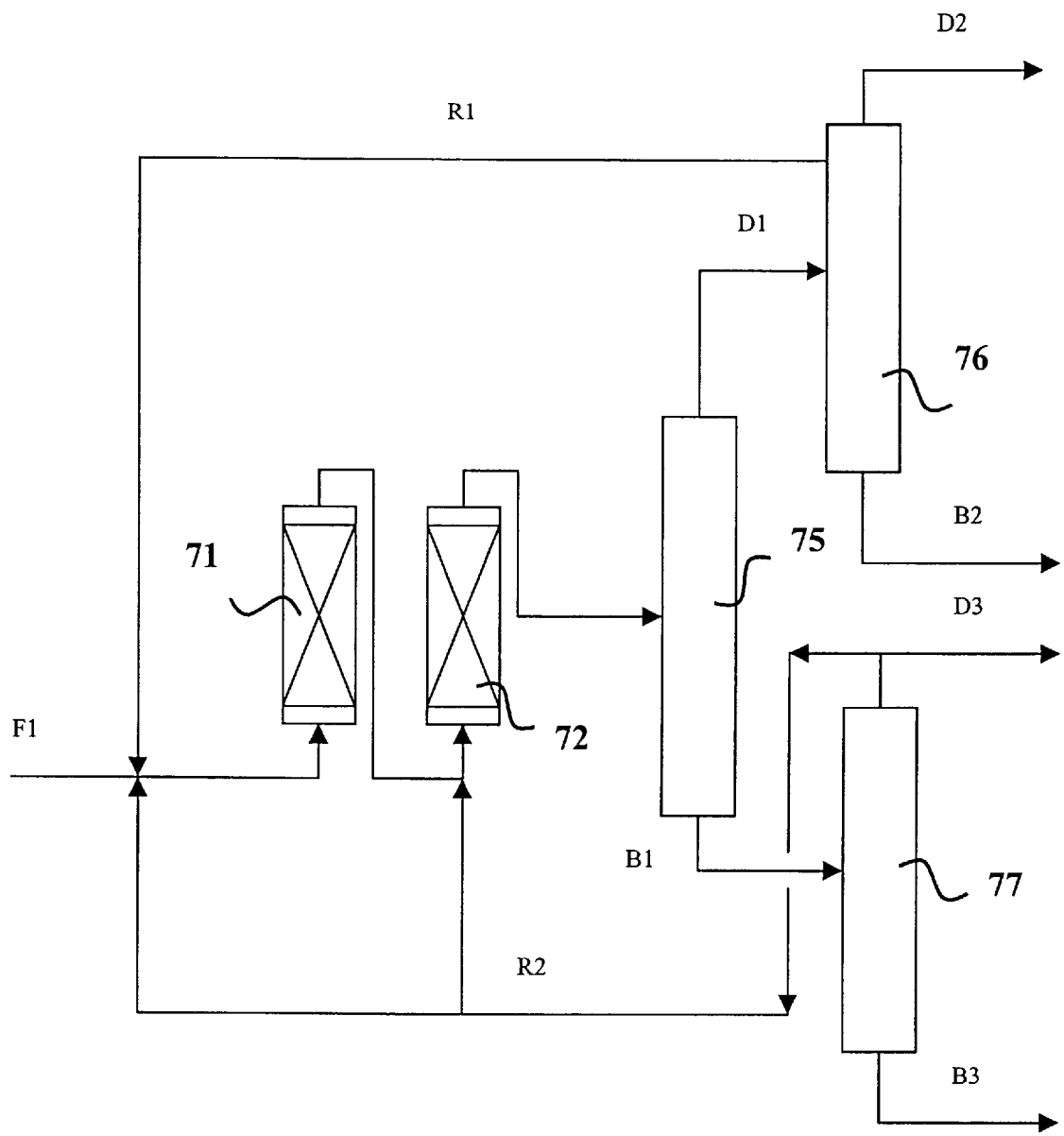
FIG. 7 depicts an embodiment in which the fractionation is carried out in three distillation columns, of which from the two first a recycling flow is conducted to dimerization.

According to a further variation of the embodiment described above the process comprises an additional distillation column in which the mixture of ethers and olefin oligomers fractionated. This kind of a process is presented in FIG. 7. The Figure shows that process now includes three distillation columns, the third 77 of which separates the ethers and olefin oligomers from each other. It can also be seen that the overhead product of the third distillation column can be circulated back to the dimerization (flow R2) or it can be recovered (flow D3).

According to still another preferred embodiment of the invention the oxygenate concentration is lower when the olefin content in the reaction zone is lower. Thus, the process is divided into two loops, and advantageously, when the oxygenate content in the reactor is relatively high (as is the case in the beginning of the process), the residence time in the reactor is remote, and when the oxygenate concentration is lower, the residence time in the reactor is longer.

The residence time in each reactor can be defined by means of the level of the conversion desired to achieve in each of the reactors. Thus, 5 to 95%, preferably 60 to 90% of the total olefin conversion is obtained in the first reaction stage and 95 to 5%, preferably 40 to 10% of the olefin conversion is obtained in the second reaction zone. Typically, LHSV would then be 0.1 to 20 h$^{-1}$, preferably 0.3 to 5 h$^{-1}$.

In general, the ratio of the oxygenate to olefin is between 0.005 and 0.7, preferably between 0.005 and 0.15 in the first reaction stage, and between 0.001 and 0.7, preferably between 0.001 and 0.1 in the second reaction stage. When isobutene is fed to the process as the olefin and water is fed to the process as the oxygenate, then the ratio of TBA (formed in the reaction between water and isobutene) to isobutene in the first reaction stage is between 0.01 and 0.5, preferably between 0.01 and 0.15 and in the second reaction stage between 0.001 and 0.5, preferably between 0.001 and 0.1. In the second reaction stage, it advantageous to operate at conditions where the ratio approaches zero.

Figure 8:
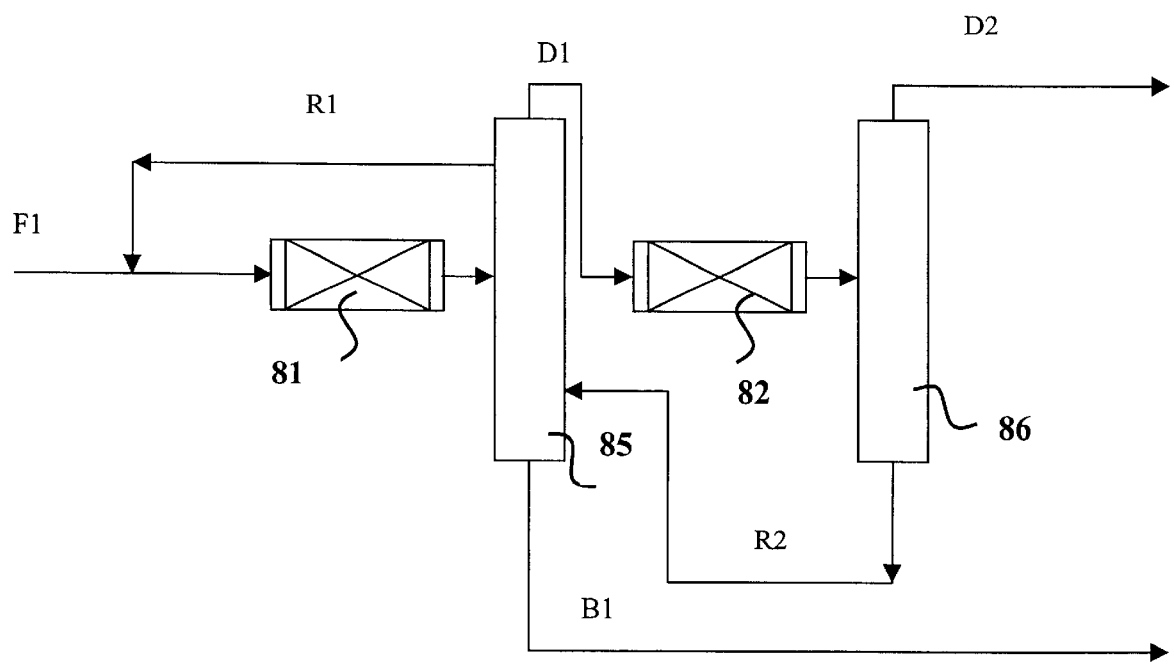
FIG. 8 depicts an embodiment in which a distillation column is placed after each reactor and from both of the distillation columns an oxygenate-containing flow is circulated back to an earlier stage of the process.

A process configuration according to the embodiment is illustrated in FIG. 8. The fresh hydrocarbon feed F1 is conducted to a first reactor 81, from which the reactor effluent is introduced into a first distillation column 85. The bottoms product B1 of the first distillation column comprises dimerized olefins which can be conducted to hydrogenation. A flow R1 containing oxygenate and possibly unreacted olefins is drawn from the side of the first distillation column, from the upper part of the column. Also unreacted olefins leave the first distillation column along with the overhead product D1. The overhead product D1 of the first distillation column 85 also contains oxygenate formed in the first reactor 81 or fed to the process separately. The overhead product D1 is then conducted to a second reactor 82. Olefins dimerize further in the presence of the oxygenate. A second distillation column 86 is used to separate inert hydrocarbons and alcohol from dimerized olefin product and ether all possibly present in the effluent of the second reactor 82. Thus, the overhead product D2 of the second distillation column 86 comprises mainly unreacted oxygenate and inert hydrocarbons, while the bottoms product R2 containing dimerized olefin and ether is circulated back to the first distillation column 85, where dimerized reaction product is separated from ether.

Optionally, the overhead product D2 of the second distillation column 86 is conducted to a recovery unit (not presented), and the oxygenate obtained therefrom may be circulated back to the fresh feed or to any one of the reactors. The most simple form of a recovery unit is a separation tank where e.g. water phase is separated from the organic phase. On the other hand, the recovery unit can also comprise a whole process unit.

In the case where the feed comprises both $C_4$- and $C_5$-hydrocarbons, the inert fractions can be separated from one another in the second distillation column, by withdrawing a side flow from the column, which sideflow comprises $C_5$- and heavier hydrocarbons while $C_4$- and lighter hydrocarbons are in the overhead of the column as described above. The oxygenate separation presented above can be carried out in one or both of the hydrocarbon flows.

EXAMPLES

Seven examples are presented in order to further illustrate the invention. Experimental kinetic studies form the basis for the six first examples. Different process configurations have then been simulated on the basis of the models obtained from the experimental results. The computational results have then been verified in a pilot plant.

The criteria for the examples have been adjusted so that feed in the four first examples is a mixture corresponding to the product of dehydrogenation. The feed comprises 45 wt-% isobutene, 50 wt-% isobutane and other inert $C_4$-hydrocarbons, 4 wt-% $C_3$- and lower hydrocarbons and 1 wt-% $C_5$- and heavier hydrocarbons.

The total hydrocarbon feed (excluding methanol) is set to be 100 000 kg/h. A 95% conversion of isobutene has also been set as a criterion.

The seventh example is an experimental example without simulation.

EXAMPLE 1

Figure 9:
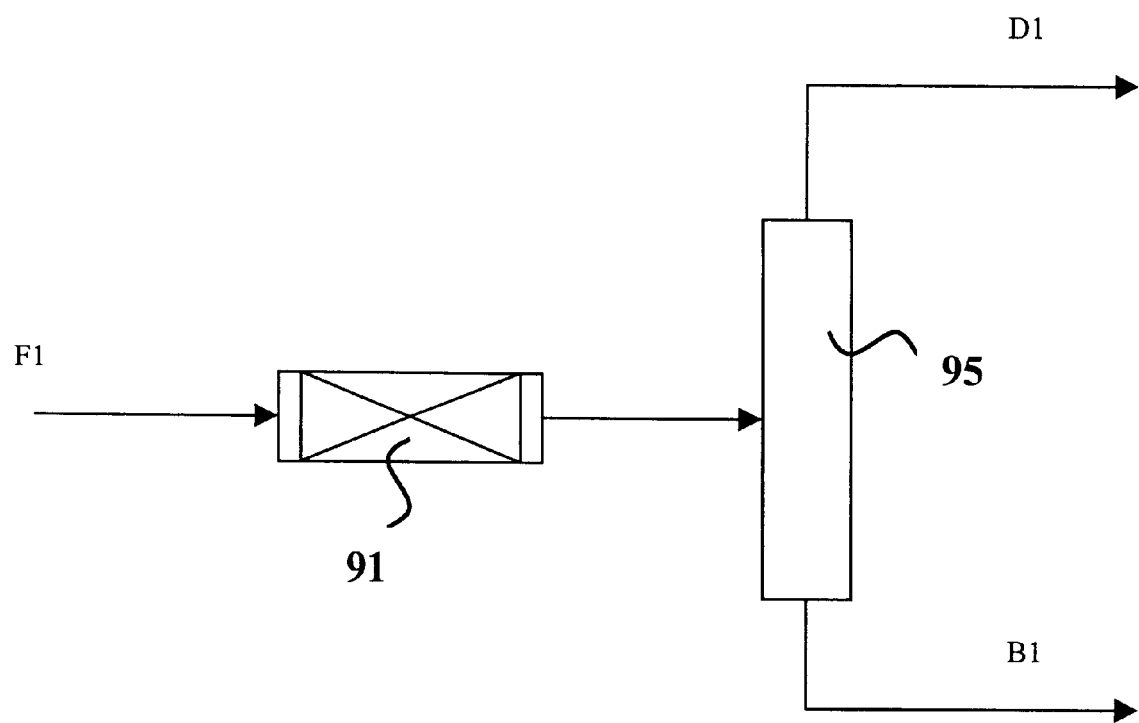
FIG. 9 depicts a process according to the prior art without circulation.

The process configuration according to FIG. 9 was simulated for producing iso-octane from a hydrocarbon feed containing isobutene. The process configuration of this example is used for simulating a process known in the art.

The molar ratio of methanol and isobutene was selected to be the minimum value given in EP-A-O 745 576, namely 0.45.

Thus, methanol is introduced to the process with a feed rate of 11751 kg/h. Since a high isobutene conversion and a high iso-octene yield are aimed at, it is necessary to use a very high amount of catalyst. The mass flows and weight fractions of each component in total feed F1 and in product flow B1 are presented in Table 1.

TABLE 1

| | F1 | | B1 | |
|---|---|---|---|---|
| Main components | Kg/h | Weight fraction | Kg/h | Weight fraction |
| Isobutene | 45000 | 0.4033 | 383.9 | 0.0070 |
| Isobutane | 50000 | 0.4481 | 4156.3 | 0.0756 |
| MeOH | 11571 | 0.1037 | 0.3 | 0.0000 |
| MTBE | 0 | 0.0000 | 13640.4 | 0.2480 |
| Dimers | 0 | 0.0000 | 30182.4 | 0.5488 |
| Trimers | 0 | 0.0000 | 3737.7 | 0.0680 |
| Tetramers | 0 | 0.0000 | 347.4 | 0.0063 |
| $C_3$-hydrocarbons | 4000 | 0.0359 | 0.2 | 0.0000 |
| $C_5$-hydrocarbons | 1000 | 0.0090 | 999.7 | 0.0182 |
| Total | 111571 | 1 | 55000 | 0.97 |

The results show that large amounts of trimers and MTBE are present in the product. If MTBE was to be decomposed completely, also a major part of iso-octene would convert to tri-isobutene and heavier oligomers.

Thus, the technology used in prior art is not applicable for producing pure iso-octene.

EXAMPLE 2

The process for producing iso-octane from a hydrocarbon flow containing isobutene was simulated using a process configuration according to FIG. 1.

The example demonstrates how iso-octene yield is increased by circulating a flow containing MTBE and methanol and unreacted isobutene back to the beginning of the process. At the same time, the product flow is of decent quality and the major part of the product flow is iso-octene.

The mass flows and weight fractions of each component in each flow are presented in Table 2.

TABLE 2

| | F1 | | R1 | | B1 | |
|---|---|---|---|---|---|---|
| Main components | Kg/h | Weight fraction | Kg/h | Weight fraction | Kg/h | Weight fraction |
| Isobutene | 45000 | 0.4425 | 20469.1 | 0.0292 | 0.1 | 0.0000 |
| Isobutane | 50000 | 0.4916 | 417994.3 | 0.5971 | 1.3 | 0.0000 |
| MeOH | 1700 | 0.0167 | 1593.9 | 0.0023 | 0.0 | 0.0000 |
| MTBE | 0 | 0 | 86973.3 | 0.1242 | 801.3 | 0.0184 |
| Dimers | 0 | 0 | 73.4 | 0.0001 | 38821.8 | 0.8925 |
| Trimers | 0 | 0 | 0.0 | 0.0000 | 3625.3 | 0.0833 |
| Tetramers | 0 | 0 | 0.0 | 0.0000 | 97.6 | 0.0022 |
| $C_3$-hydrocarbons | 4000 | 0.0393 | 3873.7 | 0.0055 | 0.0 | 0.0000 |
| $C_5$-hydrocarbons | 1000 | 0.0098 | 168845.8 | 0.2412 | 66.3 | 0.0015 |
| Total | 101700 | 1 | 700000 | 0.9998 | 43500.0 | 0.998 |

EXAMPLE 3

The process for producing iso-octane from a hydrocarbon flow containing isobutene was simulated using a process configuration according to FIG. 4.

In this embodiment, the dimers are separated from the flow passing through the reactors relatively near the beginning of the reactor sequence. The major part of the reaction occurs in the beginning of the reactor system, and thus it is possible to remove the major part of the dimers after a relatively short residence time. This way the dimers do not have the time to react further to trimers and heavier components. The flow containing MTBE is circulated back from the two latter distillation columns also in this embodiment.

The mass flows and weight fractions of each component in total feed flow and in the circulation flows are presented in Table 3.

TABLE 3

| | F1 | | R1 | | R2 | |
|---|---|---|---|---|---|---|
| Main components | Kg/h | Weight fraction | Kg/h | Weight fraction | Kg/h | Weight fraction |
| Isobutene | 45000 | 0.4484 | 6988.9 | 0.0424 | 0.0 | 0.0000 |
| Isobutane | 50000 | 0.4983 | 67402.9 | 0.4085 | 0.0 | 0.0000 |
| MeOH | 350 | 0.0035 | 480.0 | 0.0029 | 0.4 | 0.0001 |

TABLE 3-continued

|  | F1 | | R1 | | R2 | |
|---|---|---|---|---|---|---|
| Main components | Kg/h | Weight fraction | Kg/h | Weight fraction | Kg/h | Weight fraction |
| MTBE | 0 | 0.0000 | 60463.7 | 0.3664 | 2995.9 | 0.7702 |
| Dimers | 0 | 0.0000 | 847.4 | 0.0051 | 764.6 | 0.1966 |
| Trimers | 0 | 0.0000 | 0.0 | 0.0000 | 96.4 | 0.0248 |
| Tetramers | 0 | 0.0000 | 0.0 | 0.0000 | 1.5 | 0.0004 |
| $C_3$-hydrocarbons | 4000 | 0.0399 | 942.6 | 0.0057 | 0.0 | 0.0000 |
| $C_5$-hydrocarbons | 1000 | 0.0100 | 27848.4 | 0.1688 | 31.0 | 0.0080 |
| Total | 100350 | 1 | 165000 | 0.9998 | 3889.9 | 1 |

The compositions of the product flows B1 and B2 are presented in Table 4.

TABLE 4

|  | B1 | | B2 | |
|---|---|---|---|---|
| Main components | Kg/h | Weight fraction | Kg/h | Weight fraction |
| Isobutene | 0.7 | 0.0000 | 0.0 | 0.0000 |
| Isobutane | 2.3 | 0.0001 | 0.0 | 0.0000 |
| MeOH | 0.0 | 0.0000 | 0.0 | 0.0000 |
| MTBE | 401.7 | 0.0145 | 2.5 | 0.0002 |
| Dimers | 24804.1 | 0.8922 | 14828.2 | 0.9385 |
| Trimers | 2507.6 | 0.0902 | 911.9 | 0.0577 |
| Tetramers | 56.2 | 0.0020 | 17.5 | 0.0011 |
| $C_3$-hydrocarbons | 0.0 | 0.0000 | 0.0 | 0.0000 |
| $C_5$-hydrocarbons | 24.9 | 0.0009 | 0.1 | 0.0000 |
| Total | 27800 | 0.9999 | 15800 | 0.9975 |

EXAMPLE 4

The process for producing iso-octane from a hydrocarbon flow containing isobutene was simulated using a process configuration according to FIG. 8, with exception that water was separated after the second distillation column from the distillate D2 and circulated as R3 back to the fresh water feed.

In this embodiment, water is used as the oxygenate, and thus the product flows do not contain ethers at all. Instead, the reactor effluents comprise TBA and water, which are circulated back to the either one of the reactors.

The mass flows and weight fractions of each component in total feed flow and in the circulation flows are presented in Table 5.

The third circulation flow comprises water, and the mass flow is calculated to be 0.08 kg/h.

The composition of the total product flow is presented in Table 6.

TABLE 6

|  | B1 | |
|---|---|---|
| Main components | Kg/h | Weight fraction |
| Inert light hydrocarbons | 0.00 | 0.00 |
| Inert heavy hydrocarbons | 0.18 | 0.0047 |
| Isobutene | 0.00 | 0.00 |
| Dimers | 34.56 | 0.8958 |
| Heavier oligomers | 3.84 | 0.0995 |
| Water | 0.00 | 0.00 |
| IBA | 0.00 | 0.00 |
| Total | 38.58 | 1.00 |

EXAMPLE 5

The behaviour of methanol and MTBE in hindering the side reactions was examined by conducting two experiments with similar experimental settings. A mixture of isobutene (45%) and isobutane (55%) was used as feedstock.

When methanol was added in a ratio of 0.1 mol methanol per mol isobutene to the starting material mixture, a product mixture with, inter alia, 26.3% iso-octene and 10.8% was obtained at the end of the experiment.

When MTBE was added to the starting material mixture instead of methanol in a similar ratio, the mixture at the end of the experiment contained approximately 28.8% iso-octene and 11.2% tri-isobutene. Due to the relatively low concentration of the oxygen containing compound in the feedstock, the product composition can not be considered good. Nevertheless, the experiment does show that not only alcohol, but also other oxygenates hinder the oligomerization of iso-octene, partly even better than alcohol.

EXAMPLE 6

The process for dimerizing hydrocarbon feedstock containing mainly $C_5$-hydrocarbons was simulated using a process configuration according to FIG. 1. In addition, inert $C_6$-hydrocarbons and small amounts of $C_4$-olefins were present in the feed.

The example demonstrates how olefinic hydrocarbon feedstock is dimerized and from the subsequent distillation column, a recycling flow is drawn from the side of the column. The dimerized reaction product is recovered as the bottoms product of the column. Since $C_5$-olefins form the major part of the hydrocarbon feedstock, only a small

TABLE 5

|  | F1 | | F2 | | R1 | | R2 | |
|---|---|---|---|---|---|---|---|---|
| Main components | Kg/h | Weight fraction | Kg/h | Weight fraction | Kg/h | Weight fraction | Kg/h | Weight fraction |
| Inert light hydrocarbons | 59.79 | 0.5979 | 0.00 | 0 | 17.89 | 0.4501 | 0.00 | 0.0000 |
| Inert heavy hydrocarbons | 0.21 | 0.0021 | 0.00 | 0 | 16.47 | 0.4145 | 0.05 | 0.0000 |
| Isobutene | 40.00 | 0.4 | 0.00 | 0 | 2.32 | 0.0583 | 0.00 | 0.0001 |
| Dimers | 0.00 | | 0.00 | 0 | 0.01 | 0.0002 | 4.66 | 0.7702 |
| Heavier oligomers | 0.00 | | 0.00 | 0 | 0.00 | | 0.79 | 0.1966 |
| Water | 0.00 | | 0.02 | 1 | 0.12 | 0.0031 | 0.01 | 0.0248 |
| TBA | 0.00 | | 0.00 | 0 | 2.93 | 0.0738 | 0.19 | 1 |
| Total | 100.00 | 1.00 | 0.02 | 1.00 | 39.74 | 1.00 | 5.70 | | amount of oxygenate is present, both in the reaction zone and in recycling flow R1.

The amount of the recycling flow R1 is rather great, which is advantageous in view of the temperature control of the reactor.

The mass flows of each component in each flow is presented in Table 7.

TABLE 7

| Main components | F1 Kg/h | R1 Kg/h | D1 Kg/h | B1 Kg/h |
|---|---|---|---|---|
| $C_6$-hydrocarbons | 2121 | 26499 | 6 | 2114 |
| $C_5$-olefins | 63622 | 15087 | 63622 | 0 |
| $C_4$-olefins | 6853 | 303 | 6853 | 0 |
| Isoamylenes | 27259 | 1379 | 1483 | 0 |
| Oligomers | 0 | 0 | 0 | 25759 |
| $H_2O$ | 146 | 2 | 141 | 0 |
| TAA | 0 | 408 | 21 | 0 |
| Total | 100000 | 43678 | 72126 | 27874 |

The term oligomers comprises the reaction product, of which dimers form over 90%.

The treatment of the distillate D1 from the distillation column is not presented. Typically, oxygenates, i.e., water and alcohol, would be separated from the distillate D1 and recycled back to the feed of the reactor.

EXAMPLE 7

The reaction of a feed containing $C_4$- and $C_5$-olefins was carried out in a tubular reactor at approximately 85° C. with a VHSV of approximately 1 $h^{-1}$. The analysis of the reactor effluent as well as a detailed description of the feed is presented in Table 8.

TABLE 8

|  | Feed, g | Light product, g | Oligomers, g |
|---|---|---|---|
| Isobutene | 6.694 | 1.959 | 0 |
| Linear butenes | 19.475 | 14.498 | 0 |
| Other $C_4$-components | 35.573 | 35.322 | 0 |
| Isoamylenes | 8.716 | 3.091 | 0 |
| Other $C_5$-components | 28.707 | 28.190 | 0 |
| TBA | 0.834 | 0.019 | 0 |
| $C_4$-dimers | 0 | 0 | 4.820 |
| $C_4/C_5$-codimers | 0 | 0 | 7.540 |
| $C_5$-dimers | 0 | 0 | 2.320 |
| Heavier oligomers | 0 | 0 | 2.240 |
| Total | 100.000 | 83.080 | 16.920 |

Table 8 shows that most of the oligomers formed are $C_4/C_5$-codimers, i.e., $C_9$-olefins, such as tetramethylpentene and trimethylhexene. Hydrogenated branched $C_9$-olefins have a highly beneficial influence on the octane number of fuels.

The composition of the dimer fraction of the product is as follows:

25.6 wt-% trimethylpentenes, 22.3 wt-% tetramethylpentenes and trimethylhexenes, 5.4 wt-% tetramethylhexenes and 3.9 wt-% trimethylheptenes. Rest (42.4 wt-%) of the dimer product comprises other, less branched dimers.

With a process configuration according to the present invention, the product composition could be optimized.

What is claimed is:

1. A process for dimerizing olefinic hydrocarbon feedstock containing isobutene comprising feeding fresh olefinic hydrocarbon feedstock containing isobutene and oxygenate, wherein said oxygenate is water, to a reaction zone of a system including at least one reaction zone and at least one distillation zone, said at least one reaction zone comprising at least one reactor and said at least one distillation zone comprising at least one distillation column, contacting said olefinic hydrocarbon feedstock containing isobutene with an acidic ion exchange resin in said reaction zone in the presence of said oxygenate, under conditions in which at least part of the olefins dimerize and wherein said oxygenate reacts with the isobutene present in the feedstock to form tertiary butanol, conducting effluent comprising unreacted hydrocarbons, dimerized olefin product, oxygenate and tertiary butanol from said reaction zone to said distillation zone where said dimerized product is separated from said effluent, withdrawing at least one flow comprising oxygenate and tertiary butanol, which forms azeotropes with hydrocarbons present in said effluent, from the at least one distillation column and circulating said flow from said distillation zone back to the reaction zone, and recovering the dimerized product and optionally hydrogenating said dimerized product to form a parafinic dimerized product.

2. The process according to claim 1, wherein at least one sideflow is drawn from the distillation column from a plate higher than a feed plate.

3. A process for dimerizing olefinic hydrocarbon feedstock containing isobutene and $C_5$ olefins, comprising feeding fresh olefinic hydrocarbon feedstock containing isobutene and $C_5$ olefins and oxygenate, wherein said oxygenate is water, to a reaction zone of a system including at least one reaction zone and at least one distillation zone, said at least one reaction zone comprising at least one reactor and said at least one distillation zone comprising at least one distillation column, contacting said olefinic hydrocarbon feedstock containing isobutene and $C_5$ olefins with an acidic ion exchange resin in said reaction zone in the presence of said oxygenate, under conditions in which at least part of the olefins dimerize and wherein said oxygenate reacts with the isobutene present in the feedstock to form tertiary butanol, conducting effluent comprising unreacted hydrocarbons, dimerized olefin product, oxygenate and tertiary butanol from said reaction zone to said distillation zone where said dimerized product is separated from said effluent, withdrawing at least one flow comprising oxygenate and tertiary butanol, which forms azeotropes with hydrocarbons present in said effluent, from the at least one distillation column and circulating said flow from said distillation zone back to the reaction zone, and recovering the dimerized product and optionally hydrogenating said dimerized product to form a parafinic dimerized product.

4. The process according to claim 3, wherein the other olefins present in the olefinic feedstock are selected from the group consisting of 1-butene, 2-butene, and linear and branched C5 olefins, and mixtures thereof.

5. The process according to claim 1, wherein the temperature is increased during the reaction.

6. The process according to claim 1, wherein essentially no fresh oxygenate is fed to the reaction zone.

7. The process according to claim 1, further comprising feeding fresh oxygenate into the reaction zone.

8. The process according to claim 3, wherein the olefins present in the olefinic feedstock are selected from the group consisting of linear and branched C5 olefins, and mixtures thereof.

9. The process according to claim 8, wherein the linear and branched C5 olefins are selected from the group consisting of linear pentene, 2-methyl-1-butene, 2-methyl-2-butene and 3-methyl-1-butene.

10. The process according to claim 4, wherein the linear and branched C5 olefins are selected from the group consisting of linear pentene, 2-methyl-1-butene, 2-methyl-2-butene and 3-methyl-1-butene.

11. A process for dimerizing olefinic hydrocarbon feedstock containing isobutene, comprising:

feeding fresh olefinic hydrocarbon feedstock containing isobutene and oxygenate, wherein said oxygenate is water, to a reaction zone of a system including at least one reaction zone and at least one distillation zone, said at least one reaction zone comprising at least one reactor and said at least one distillation zone comprising at least one distillation column, contacting said olefinic hydrocarbon feedstock containing isobutene with an acidic ion exchange resin in the reaction zone in the presence of said oxygenate under conditions in which at least a part of the olefins dimerize and wherein the oxygenate reacts with the isobutene in the feedstock to form tertiary butanol and wherein the tertiary butanol forms an azeotrope with the olefins, conducting effluent comprising unreacted hydrocarbons, dimerized reaction product, oxygenate and tertiary butanol from said reaction zone to said distillation zone where dimerized reaction product is separated from said effluent in the presence of a compound which breaks the azeotropes formed in the reaction zone, withdrawing at least one flow comprising tertiary butanol which forms azeotropes with hydrocarbons present in said effluent from the at least one distillation column and circulating said flow from said distillation zone back to the reaction zone, and recovering the dimerized product and optionally hydrogenating said dimerized product to form a parafinic reaction product.

12. A process for producing iso-octane from hydrocarbon feedstock containing isobutene and C5 olefins, comprising:

feeding fresh olefinic feedstock containing isobutene and C5 olefins and oxgenate, wherein said oxygenate is water to a reaction zone of a system including at least one reaction zone and at least one distillation zone, said at least one distillation zone comprising at least one reactor and said at least one distillation zone comprising at least one distillation column, contacting said hydrocarbon feedstock containing isobutene and C5 olefins with an acidic ion exchange resin in the reaction zone in the presence of said oxygenate under conditions in which at least part of the isobutene dimerizes to iso-octene and wherein said oxygenate reacts with the isobutene present in the feedstock to form tertiary butanol, conducting effluent comprising unreacted hydrocarbons, iso-octene, oxygenate and tertiary butanol from said reaction zone to said distillation zone where iso-octene is separated from the effluent, withdrawing a flow comprising oxygenate and tertiary butanol from the at least one distillation column and circulating said flow from said distillation column back to the reaction zone, recovering the obtained iso-octene and optionally hydrogenating it further to iso-octane.

13. A process for dimerizing olefinic hydrocarbon feedstock containing isobutene and C5 olefins, comprising:

feeding fresh olefinic hydrocarbon feedstock containing isobutene and C5 olefins and oxygenate, wherein said oxygenate is water, to a reaction zone of a system including at least one reaction zone and at least one distillation zone, said at least one reaction zone comprising at least one reactor and said at least one distillation zone comprising at least one distillation column, contacting said olefinic hydrocarbon feedstock containing isobutene and C5 olefins with an acidic ion exchange resin in the reaction zone in the presence of said oxygenate under conditions in which at least a part of the olefins dimerize and wherein the oxygenate reacts with the isobutene in the feedstock to form tertiary butanol and wherein the tertiary butanol forms an azeotrope with few olefins, conducting effluent comprising unreacted hydrocarbons, dimerized reaction product, oxygenate, and tertiary butanol to said distillation zone where dimerized reaction product is separated from said effluent in the presence of a compound which breaks the azeotropes formed in the reaction zone, withdrawing at least one flow comprising tertiary butanol which forms azeotropes with hydrocarbons present in said effluent from the at least one distillation column and circulating said flow from said distillation zone back to the reaction zone, and recovering the dimerized product and optionally hydrogenating said dimerized product to form a parafinic reaction product.

14. The process according to claim 1, wherein the olefin(s) are dimerized in two reaction stages, of which in the first stage the ratio of oxygenate to olefin is higher and the residence time remote in the reactor, and in the second stage the ratio of oxygenate to olefin is low in the reactor and the residence time is longer.

15. The process according to claim 14, wherein the ratio of oxygenate to olefin in the first stage is 0.01–0.7 and in the second stage 0.001–0.5.

16. The process according to claim 15, wherein the ratio of oxygenate to olefin in the first stage is 0.01–0.15 and in the second stage 0.001–0.1.

17. The process according to claim 16, wherein the temperature in the second reactor is higher than the temperature in the first reactor.

18. The process according to claim 1, wherein unreacted hydrocarbons are recovered as the overhead product of the distillation zone, and then conducted to alcohol recovery to recover alcohol and hydrocarbons, after which alcohol is circulated to the dimerization reaction.

19. A process for producing iso-octane from hydrocarbon feedstock containing isobutene, comprising:

feeding fresh olefinic feedstock containing isobutene and oxgenate, wherein said oxygenate is water to a reaction zone of a system including at least one reaction zone and at least one distillation zone, said at least one distillation zone comprising at least one reactor and said at least one distillation zone comprising at least one distillation column, contacting said hydrocarbon feedstock with an acidic ion exchange resin in the reaction zone in the presence of said oxygenate under conditions in which at least part of the isobutene dimerizes to iso-octene and wherein said oxygenate reacts with the isobutene present in the feedstock to form tertiary butanol, conducting effluent comprising unreacted hydrocarbons, iso-octene, oxygenate and tertiary butanol from said reaction zone to said distillation zone where iso-octene is separated from the effluent, withdrawing a flow comprising oxygenate and tertiary butanol from the at least one distillation column and circulating said flow from said distillation column back to the reaction zone, recovering the obtained iso-octene and optionally hydrogenating it further to iso-octane.

20. The process according to claim 19, wherein at least 80% of the formed isobutene oligomers are isobutene dimers.

21. The process according to claim 19, wherein at least two flows are withdrawn from the at least one column.

22. The process according to claim 19, wherein the flow is drawn from the distillation column from a plate higher than a feed plate.

23. The process according to claim 19, wherein the temperature is increased during the reaction.

24. The process according to claim 19, further comprising feeding fresh oxygenate into the reaction zone.

25. A process for dimerizing fresh olefinic hydrocarbon feedstock containing isobutene and C5 olefins, comprising:

feeding fresh olefinic hydrocarbon feedstock containing isobutene and C5 olefins and oxygenate, wherein said oxygenate is water to a reaction zone of a system including at least one reaction zone and at least one distillation zone, said at least one reaction zone comprising at least one reactor and said at least one distillation zone comprising at least one distillation column, contacting said olefinic hydrocarbon feedstock with an acidic ion exchange resin in the reaction zone in the presence of said oxygenate under conditions at which at least a part of the olefins dimerize and wherein the oxygenate reacts with the isobutene present in the feedstock to form tertiary butanol, conducting effluent comprising unreacted hydrocarbons, dimerized olefinic product, oxygenate and tertiary butanol to said distillation zone where dimerized product is separated from said effluent, drawing a flow comprising oxygenate and tertiary butanol from the at least one distillation column and circulating said flow from said distillation zone to the reaction zone, circulating the unreacted hydrocarbons of said distillation column back to dimerization, and recovering the obtained dimerized product to form a parafinic reaction product.

26. The process according to claim 25, wherein the olefins present in the olefinic feedstock are selected from the group consisting of linear and branched C5 olefins, and mixtures thereof.

27. The process according to claim 25, wherein the other olefins present in the feedstock are selected from the group consisting of 1-butene, 2-butene, and linear and branched C5 olefins, and mixtures thereof.

28. The process according to claim 11, wherein the azeotrope-breaking compound is incorporated into the feed.

29. The process according to claim 11, wherein the azeotrope-breaking compound is a $C_6$ hydrocarbon.

30. A fuel component comprising iso-octane (2,2,4-trimethylpentane) and having an octane number (RON) of at least 95, said component comprising 10–6 wt-% hydrogenated isobutene trimers and
at least 85 wt-% trimethylpentanes, of which
at least 65 wt-% iso-octane.

31. The process according to claim 19, wherein the olefin(s) are dimerized in two reaction stages, of which in the first stage the ratio of oxygenate to olefin is higher and the residence time remote in the reactor, and in the second stage the ratio of oxygenate to olefin is low in the reactor and the residence time is longer.

32. The process according to claim 31, wherein the ratio of oxygenate to olefin in the first stage is 0.005–0.7 and in the second stage 0.001–0.5.

33. The process according to claim 32, wherein the ratio of oxygenate to olefin in the first stage is 0.005–0.15 and in the second stage 0.001–0.1.

34. The process according to claim 33, wherein the temperature in the second reactor is higher than the temperature in the first reactor.

35. The process according to claim 19, wherein unreacted hydrocarbons are recovered as the overhead product of the distillation zone, and then conducted to alcohol recovery to recover alcohol and hydrocarbons, after which alcohol is circulated to the dimerization reaction.

36. A process for dimerizing fresh olefinic hydrocarbon feedstock containing isobutene, comprising:

feeding fresh olefinic hydrocarbon feedstock containing isobutene and oxygenate, wherein said oxygenate is water to a reaction zone of a system including at least one reaction zone and at least one distillation zone, said at least one reaction zone comprising at least one reactor and said at least one distillation zone comprising at least one distillation column, contacting said olefinic hydrocarbon feedstock with an acidic ion exchange resin in the reaction zone in the presence of said oxygenate under conditions at which at least a part of the olefins dimerize and wherein the oxygenate reacts with the isobutene present in the feedstock to form tertiary butanol, conducting effluent comprising unreacted hydrocarbons, dimerized olefinic product, oxygenate and tertiary butanol to said distillation zone where dimerized product is separated from said effluent, drawing a flow comprising oxygenate and tertiary butanol from the at least one distillation column and circulating said flow from said distillation zone to the reaction zone, circulating the unreacted hydrocarbons of said distillation column back to dimerization, and recovering the obtained dimerized product to form a parafinic reaction product.

37. The process according to claim 36, wherein the flow is drawn from the distillation column from a plate higher than the feed plate.

38. The process according to claim 36, wherein the olefins present in the olefinic feedstock are selected from the group of 1-butene, 2-butene, isobutene and mixtures thereof.

39. The process according to claim 26, wherein the linear and branched C5 olefins are selected from the group consisting of linear pentene, 2-methyl-1-butene, 2-methyl-2-butene and 3-methyl-1-butene.

40. The process according to claim 27, wherein the linear and branched C5 olefins are selected from the group consisting of linear pentene, 2-methyl-1-butene, 2-methyl-2-butene and 3-methyl-1-butene.

41. The process according to claim 36, wherein the temperature is increased during the reaction.

42. The process according to claim 36, wherein essentially no fresh oxygenate is fed to the reaction zone.

43. The process according to claim 36, wherein fresh oxygenate is fed to the reaction zone.

44. The fuel component according to claim 30, comprising
- 8–6 wt-% hydrogenated isobutene trimers and
- at least 90 wt-% trimethylpentanes, of which
    - at least 65 wt-% iso-octane.

45. The fuel component according to claim 44, characterized in that at least 85 wt-%.

46. The fuel component according to claim 45 wherein at least 95 wt-% is iso-octane.

47. A fuel component comprising
- at least 65 wt-% hydrogenated $C_5$-dimers,
- 32–5 wt-% hydrogenated olefin trimers,
- less than 1 wt-% hydrogenated olefin tetramers, and
- 2–0.01 wt-% oxygenate.

48. A fuel component comprising
- at least 50 wt-% hydrogenated dimerized olefins, of which
    - 30–20 wt-% trimethylpentanes,
    - 30–20 wt-% tetramethylpentanes and trimethylhexanes,
    - less than 10 wt-% tetramethylhexanes and
    - less than 5 wt-% trimethylheptanes,
- 28.5–5 wt-% trimers,
- less than 0.5 wt-% tetramers, and
- 1–0.01 wt-% oxygenate.

49. The fuel component according to claim 48, wherein the oxygenate is TBA.

50. The process according to claim 36, wherein unreacted hydrocarbons are recovered as the overhead product of the distillation zone, and then conducted to alcohol recovery to recover alcohol and hydrocarbons, after which alcohol is circulated to the dimerization reaction.

51. A hydrocarbon composition comprising
- at least 85 wt-% iso-octene,
- 10–6 wt-% isobutene trimers,
- less than 1 wt-% isobutene tetramers, and
- 2–0.02 wt-% MTBE.

52. The hydrocarbon composition according to claim 51, comprising
- at least 90 wt-% iso-octene,
- 8–6 wt-% isobutene trimers,
- 0–2 wt-% isobutene tetramers, and
- 1–0.02 wt-% methyl-tert-butylalcohol, MTBE.

53. A hydrocarbon composition comprising
- at least 65 wt-% dimerized $C_5$-olefins,
- 32–5 wt-% trimers,
- less than 1 wt-% tetramers, and
- 2–0.01 wt-% oxygenate.

54. A hydrocarbon composition, comprising
- at least 50 wt-% dimerized olefins, of which
    - 30–20 wt-% are trimethylpentenes,
    - 30–20 wt-% are tetramethylpentenes and trimethylhexenes,
    - less than 10 wt-% are tetramethylhexenes and
    - less than 5 wt-% are trimethylheptenes,
- 28.5–5 wt-% trimers,
- less than 0.5 wt-% tetramers, and
- 1–0.01 wt-% oxygenate.

\* \* \* \* \*